US00PP28518P2

(12) United States Plant Patent
Oudolf

(10) Patent No.: US PP28,518 P2
(45) Date of Patent: Oct. 10, 2017

(54) *PANICUM* PLANT NAMED 'PURPLE TEARS'

(50) Latin Name: *Panicum virgatum*
Varietal Denomination: Purple Tears

(71) Applicant: Green Elite Collection B.V., Lisserbroek (NL)

(72) Inventor: Piet Oudolf, Hummelo (NL)

(73) Assignee: GREEN ELITE COLLECTION BV, Lisserbroek (NL)

( * ) Notice: Subject to any disclaimer, the term of this patent is extended or adjusted under 35 U.S.C. 154(b) by 0 days.

(21) Appl. No.: 14/999,571

(22) Filed: May 26, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Penny J. Aguirre

(57) ABSTRACT

A new cultivar of *Panicum* named 'Purple Tears' that is characterized by its plant height of 120 cm, its flowering spikes that have gray color at the top, its seed heads that are purple in color and its upright plant habit.

1 Drawing Sheet

Botanical classification: *Panicum virgatum.*
Varietal denomination: 'Purple Tears'.

BACKGROUND OF THE INVENTION

The present invention relates to a new and distinct cultivar of *Panicum virgatum* and will be referred to hereafter by its cultivar name, 'Purple Tears'. 'Purple Tears' represents a new cultivar of switchgrass, an ornamental grass grown for landscape use.

The Inventor discovered 'Purple Tears' in a nursery plot in Hummelo, Netherlands in the summer of 2011. Although the parentage is unknown, *Panicum virgatum* 'Shenandoah' (not patented) is thought to be a likely parent based on the characteristics of 'Purple Tears' and its proximity in the same growing area.

Asexual propagation of the new cultivar was first accomplished by division in Hummelo, Netherlands in 2012 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Purple Tears' as a unique cultivar of *Panicum.*

1. 'Purple Tears' exhibits a plant height of 120 cm.
2. 'Purple Tears' exhibits flowering spikes that have gray color at the top.
3. 'Purple Tears' exhibits seed heads that are purple in color.
4. 'Purple Tears' exhibits an upright plant habit.

'Shenandoah', the probable parent of 'Purple Tears', differs from 'Purple Tears' in having foliage that is darker green in color and in having foliage that turns orange to red in color in the late summer. 'Purple Tears' can be most closely compared to cultivars, 'Dallas Blues' (U.S. Plant Pat. No. 11,202), and 'Rehbraun' (not patented). 'Dallas Blues' differs from 'Purple Tears' in having flowering spikes that are larger and light yellow in color, in having a taller plant height and in having leaves that are larger and more gray in color. 'Rehbraun' differs from 'Purple Tears' in having a looser plant habit, in being taller in size and in having more yellow-orange fall color.

BRIEF DESCRIPTION OF THE DRAWING

The accompanying photographs were taken in October and illustrate the characteristics of a 4 year-old plant as grown in a garden in Hummelo, Netherlands. The photograph depicts the plant habit and foliage coloration of 'Purple Tears' in bloom (plant towards back of photo). The colors in the photograph may differ slightly from the color values cited in the detailed botanical description, which accurately describe the colors of the new *Panicum.*

DETAILED BOTANICAL DESCRIPTION

The following is a detailed description of one-year-old plants of the new cultivar as grown in two-gallon containers in Rougemont, N.C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From August to September.
*Plant type.*—Herbaceous perennial grass.
*Plant habit.*—Low clump of foliage with tall flowering spikes held upright.
*Height and width or spread.*—Up to 120 cm in height and 50 cm in spread.
*Hardiness zone.*—At least in U.S.D.A. Zone 4.
*Diseases and pests.*—None have been observed.
*Root description.*—Fibrous, deep rooted.

*Propagation*.—Culm division.

*Growth rate*.—Moderate.

Culm (stem) description:

*General*.—Cylindrical, hollow pith, thin but strong, held erect.

*Culm number*.—60 in a 2-gallon container, forming tight clump.

*Culm color*.—Color between 138A and 144C in summer with very base suffused with N186C (retained into fall), 158A in winter, ranges from 8 mm to 3 cm of exposed area between leaf nodes.

*Culm size*.—Average of 3 mm in diameter, an average of 35 cm in height from the base to the base of the peduncle.

*Culm surface*.—Glabrous.

*Internode length*.—An average of 7.5 cm.

Foliage description:

*Leaf shape*.—Narrowly lanceolate.

*Leaf division*.—Simple.

*Leaf margin*.—Entire, slightly scabrous.

*Leaf base*.—Sheathed to base of the node.

*Leaf venation*.—Parallel, not distinguishable in color from leaf coloration.

*Leaf width*.—Average of 9 mm at widest section.

*Leaf length*.—Blade; an average of 25 cm, sheathed portion; an average of 7.5 cm.

*Leaves per culm*.—Average of 45 on flowering culms.

*Leaf surface*.—Glabrous and dull on both surfaces.

*Ligule*.—2 mm in width, hairy on inner surface, 158B in color on both surfaces.

*Leaf color* (*both surfaces*).—A color between 147B and 137B.

Flower description:

*Inflorescence type*.—Airy panicle at terminus of stem, primarily symmetrical, 2-flowered spikelet with lower spikelets male and upper spikelets hermaphrodite, overall color of the raceme is 148B in early summer and maturing to a blend of 138A and tinged with 187A in late summer.

*Inflorescence size*.—Average of 30 cm in length (to base of peduncle) and 26 cm in width.

*Inflorescence number*.—About 30 in a one-gallon container with new flowering spikes emerging.

*Spikelet description*.—Average of 130 per panicle, awnless, lower glume 3 mm in length and 1.5 mm in width, upper glume and lower lemma about 5 mm in length and 1.5 mm in width, glumes and lower lemma are convex with both surfaces glabrous surface and 138C in color and suffused with 187B, upper lemma is translucent and satiny, an average of 2.5 mm in length and 1.5 mm width and 145D in color.

*Spikelet size*.—About 5 mm in length and 2 mm in width.

*Rachis*.—An average of 10 cm from last leaf to panicle portion with panicle portion an average of 30 cm in length, 2 mm at base and 0.3 mm at apex in width, slightly glaucous surface, 138A in color, lateral branches (peduncle-like); an average of 10, 0.2 mm in width and up to 15 cm in length, with 1 to 2 secondary branches an average of 4.5 cm in length and 0.2 cm in width, glabrous surface, 138A in color, pedicel; an average of 4 mm in length, 0.2 mm in width, wiry, 138A in color, glabrous surface.

Reproductive organs:

*Androecium*.—Anthers; 3, 1.5 mm in length and 0.5 mm in width, N200A in color, basifixed on very fine filament, no pollen was observed.

*Gynoecium*.—Pistil; 1, 2 plumose stigmas on short, fine colorless style, stigma color is 77A, 1 mm in length and width, ovary; 1-locular, superior, 0.5 mm in length, 144D in color.

It is claimed:

1. A new and distinct cultivar of *Panicum* plant named 'Purple Tears' as herein illustrated and described.

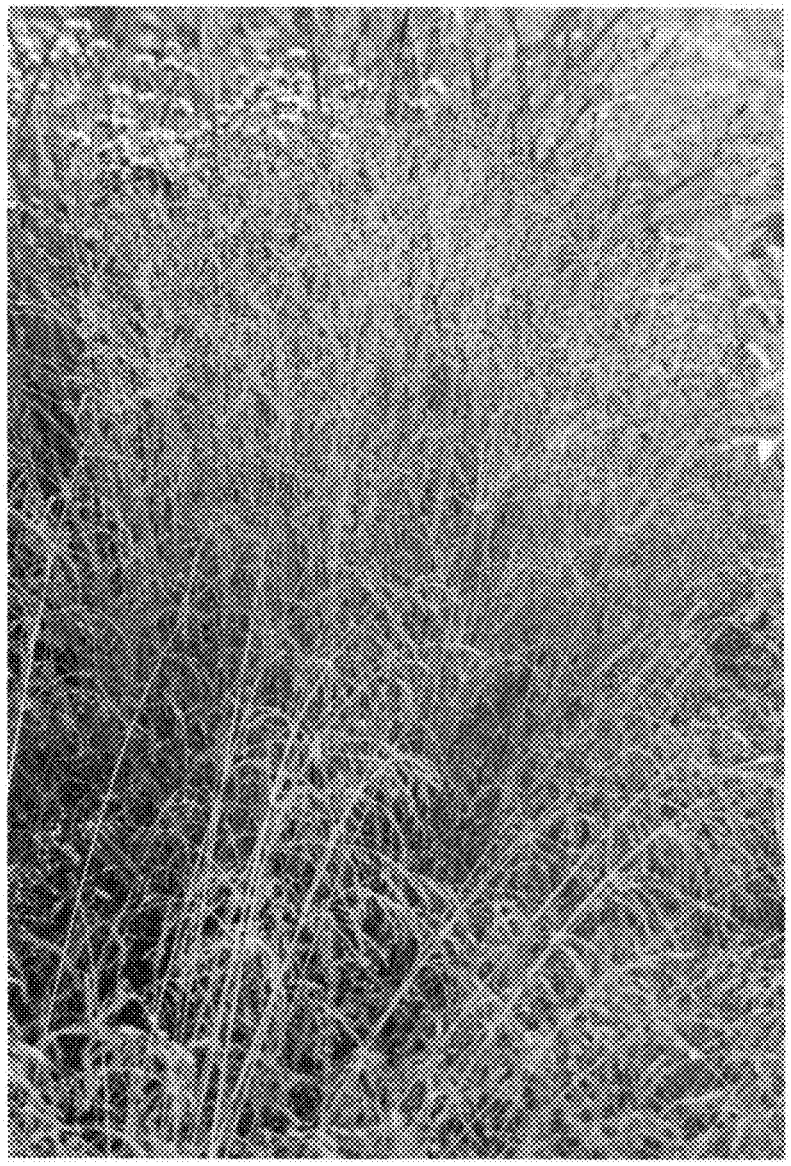

* * * * *